United States Patent [19]

Kasdan et al.

[11] Patent Number: 6,141,624
[45] Date of Patent: Oct. 31, 2000

[54] FLUID SAMPLE FOR ANALYSIS CONTROLLED BY TOTAL FLUID VOLUME AND BY TOTAL PARTICLE COUNTS

[75] Inventors: Harvey Lee Kasdan, Van Nuys; Sanford Widran, Studio City, both of Calif.

[73] Assignee: International Remote Imaging Systems, Chatsworth, Calif.

[21] Appl. No.: 08/855,107

[22] Filed: May 13, 1997

[51] Int. Cl.[7] .................................................. G01N 33/48
[52] U.S. Cl. ............................................................ 702/23
[58] Field of Search ................................ 702/23, 21, 19, 702/25; 356/335, 336

[56] References Cited

U.S. PATENT DOCUMENTS

| | | | |
|---|---|---|---|
| 4,338,024 | 7/1982 | Bolz et al. | 356/23 |
| 4,706,207 | 11/1987 | Hennessey et al. | 702/21 |
| 4,933,884 | 6/1990 | Lorenz | 702/21 |
| 4,981,362 | 1/1991 | DeJong et al. | 356/436 |
| 5,187,673 | 2/1993 | Carver, Jr. et al. | 702/21 |
| 5,457,526 | 10/1995 | Kosaka | 356/72 |
| 5,469,251 | 11/1995 | Kosaka et al. | 356/73 |
| 5,880,835 | 3/1999 | Yamazaki et al. | 356/336 |

*Primary Examiner*—Tod R. Swann
*Assistant Examiner*—Matthew Smithers
*Attorney, Agent, or Firm*—Ronald L. Yin; Limbach & Limbach LLP

[57] ABSTRACT

A fluid sample contains a plurality of different types of particles of interest. The method sets a limit for the maximum volume of the fluid sample to be analyzed, a limit for each of the different plurality of particle types, and a limit for the maximum number of particles to be analyzed with the maximum number being less than the sum of the limits for each of the different types. In the method, an aliquot of the fluid sample including the particles therein are analyzed to determine the type of the particles. The total volume of aliquots analyzed is counted. The method is stopped in the event the total of aliquots counted equals or exceeds the limit for the maximum value. For each type of particle in the fluid sample determined, a test is made if the total number of particles determined equals or exceeds the limit for each particle type. If the number does not exceed the individual type, the number of particles for that type is added and is counted. The total number of particles for all the types is counted. The method is also stopped in the event the total number of particles counted equals or exceeds the limit set. The process continues by taking another aliquot of volume. In this manner, selected emphasis of particles of interest from a fluid sample can be made.

35 Claims, 4 Drawing Sheets

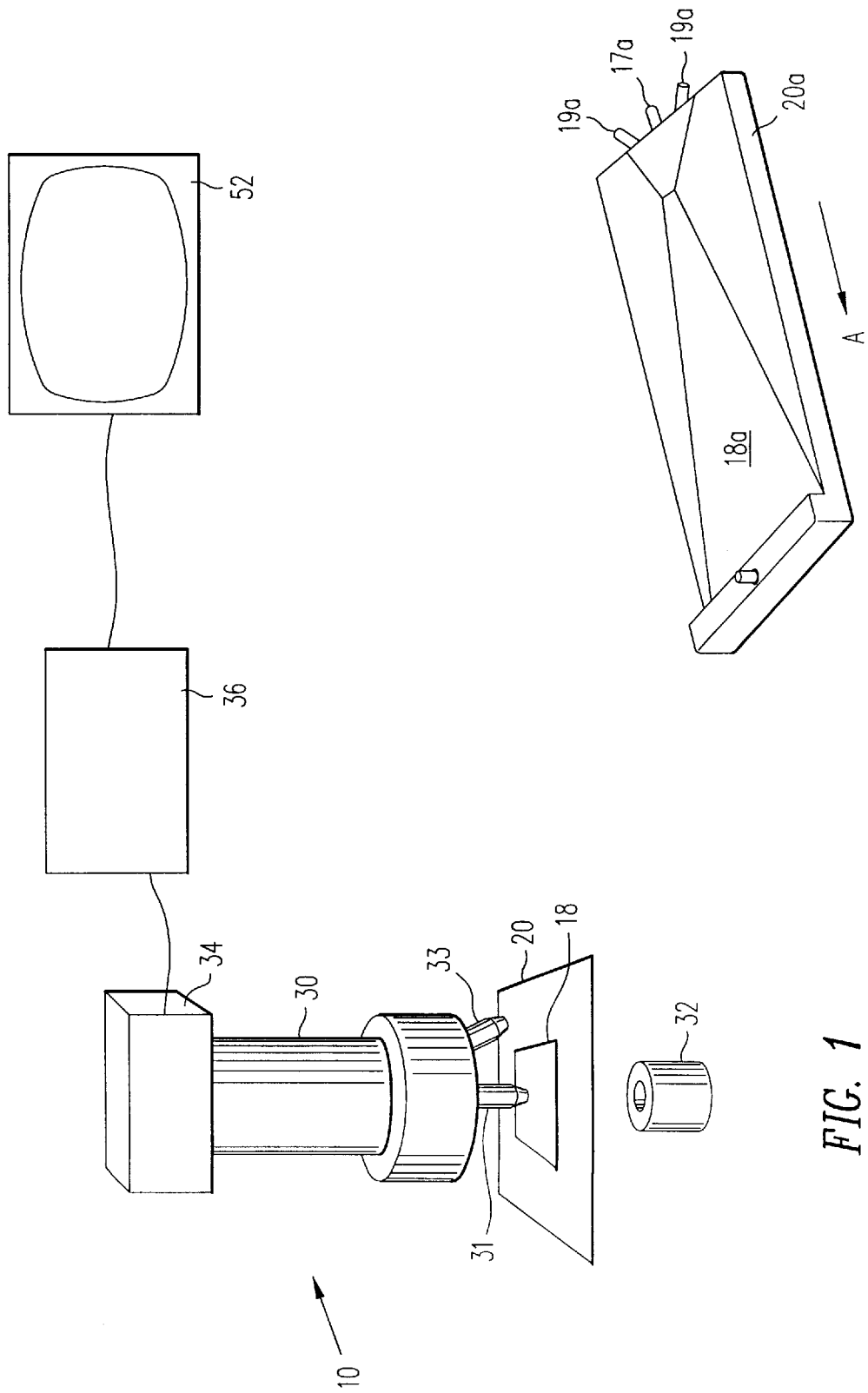

FLUID SAMPLE FOR ANALYSIS CONTROLLED BY TOTAL FLUID VOLUME AND BY TOTAL PARTICLE COUNTS

TECHNICAL FIELD

The present invention relates to a method, an apparatus, and an article of manufacture for analyzing different types of particles in a fluid sample, such that particular type or types of particles of interest may be selectively emphasized for analysis.

BACKGROUND OF THE INVENTION

Methods and apparatuses for processing images and in particular images of biological particles in a fluid sample are well known in the art. See, for example, U.S. Pat. Nos. 4,667,335 and 4,612,614 assigned to the present assignee. In those prior art references, the apparatus uses a computer having a software program to determine various characteristics of particles and in particular biological particles under examination in an imaging signal. Thus, for example, various characteristics such as color, size, concentration, etc. can be determined by the processor. The processor then uses an algorithm incorporated in its software, to identify or classify each particle based upon the characteristics determined.

In the prior art, a portion of a fluid sample is analyzed. The number of particles determined in that portion is counted. Another portion is then analyzed, and the number of particles determined from that portion is added to the total counted. This process continues until a maximum amount of time for the fluid sample flowing through a flow cell at a substantially constant volume rate is reached or a maximum number of particles is counted. The former corresponds to a maximum volume of the fluid sample being analyzed, whereas the latter corresponds to a maximum concentration.

The problem with this prior art method is that if there are a plurality of different types of particles in a fluid sample, and almost always for biological fluid samples, there are, certain types of particles occurring in low concentration, may not be observed by this method. This is because, if the maximum volume is set low, to encourage greater throughput, the method of prior art invariably causes the method to stop after the larger concentration type of particles is observed.

BRIEF DESCRIPTION OF DRAWINGS

FIG. 1 is a perspective view of an apparatus of this invention.

FIG. 2 is a perspective view of a flow chamber suitable for use with the apparatus of FIG. 1.

DETAILED DESCRIPTION OF THE INVENTION

Figure 3:
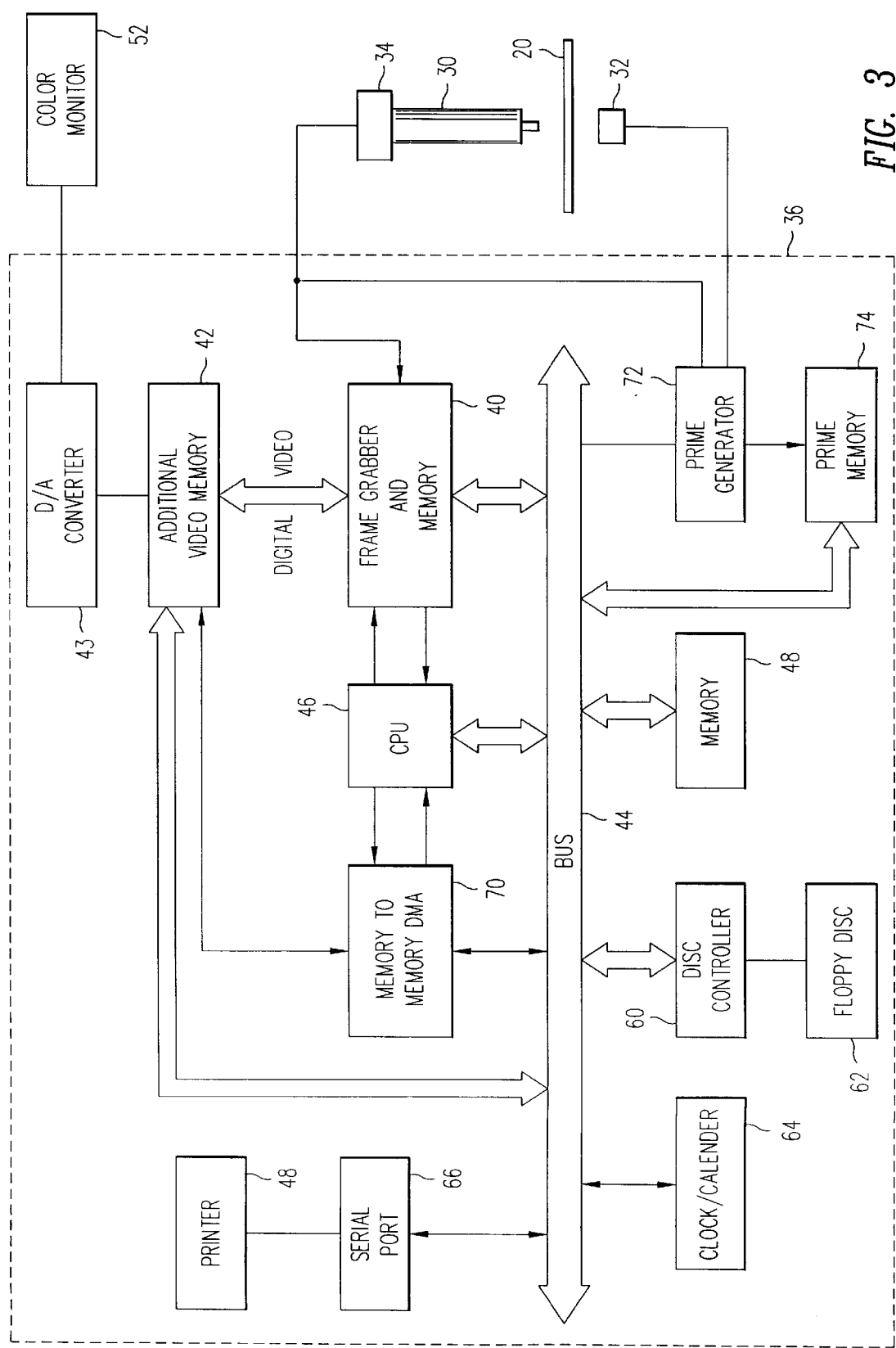
FIG. 3 is a schematic block diagram of the apparatus of FIG. 1.

An apparatus 10 of the present invention is shown in FIG. 1. The apparatus 10 includes a microscope 30 which is focused on an examination area 18 of the microscope slide 20. The examination area 18 is illuminated from below by a strobe light 32. The light 32 is directed at the microscope 30 in a direction substantially parallel to the thickness of the slide 20. The strobe light 32 provides a periodic short duration light pulse, preferably one microsecond in duration, at a rate of one-sixtieth of a second, thereby forming a series of still optical images at the microscope 30. The output of the microscope 30 is focused on a CCD camera 34 which converts the optical image focused thereon into an electronic image. After each optical image, the slide 20 is moved so that another examination area 18 is illuminated by the light 32. In this manner, a plurality of optical images are taken.

The analog-to-digital converter associated with the camera 34 also segments each of the electronic images into a plurality of pixels, with each pixel corresponding to a defined portion of each image.

Since biological particles can be examined in the examination area 18 of the microscope slide 20, a plurality of electronic images (each optical images is converted into an electronic image) contain images of the particles.

The electronic images are then passed from the camera 34 to the processor 36. The processor 36 processes each electronic image for display on display 52.

Alternatively, a flow cell 20a shown in FIG. 2 can be used in place of the microscope slide 20. The flow cell 20a is of the type fully described in U.S. Pat. No. 4,338,024. A fluid, such as urine or blood, is sent into the flow cell 20a through first input 17a. Sheath fluids are provided to the flow cell 20a through the second inputs 19a. The fluid sample is moved through the flow cell 20a in the direction shown by arrow A. The fluid sample is distributed over an extended area 18a, which has a width many times the thickness, with each measured perpendicular to the direction of flow. The fluid sample is distributed such that the particles substantially do not overlap one another in the extended area 18a. The fluid sample in the flow cell 20a is placed under the microscope 30 with the microscope 30 focused on the extended area 18a. As the fluid sample moves through the flow cell 20a, the microscope 30 takes an optical image of the fluid in the viewing area 18a. Since the fluid is moving, the apparatus 10 is held stationery. Thus, the images formed at the microscope 30 are of different portions of the fluid sample.

The processor 36 is shown in greater detail in block schematic form in FIG. 3.

The processor 36 includes a Frame Grabber and Memory 40 which receives the electronic image from the camera 34. The output of the Frame Grabber and Memory 40 is supplied to an Additional Refresh Video Memory 42, which is a memory dedicated to refreshing the video signal provided to a color monitor 52. The output of the Video Memory 42 is connected to a D/A converter 43 which is coupled to the color monitor 52.

The Frame Gabber and Memory 40 is also coupled to a Bus 44 and to a Central Processing Unit 46.

Memory 48 is also connected to the Bus 44. In addition, a disc controller 60, with a floppy disc drive 62 attached thereto, is also connected to the Bus 44. The processor 36 also comprises a clock/calendar 64 connected to the Bus 4. A serial port 66 with a printer 68 are also connected to the Bus 44. A Memory-to-Memory DMA 70 connects the Additional Video Memory 42 to the Bus 44. A prime generator 72 with a prime memory 74 are also connected to the Bus 44. The prime generator 72 also activates the strobe 32.

The display 52 can be a unit manufactured by Elo-Graphics, Inc. Such a display unit 52 has a touch screen, i.e., the display screen can accept tactile feedback signal(s) from the user. When the images of the particles are displayed, the user can edit the display. This is accomplished by touching the touch screen in the particular area where the image of the particle is to be edited. The processor 36 acknowledges the activation of the screen 52 by the user.

Figure 4A:
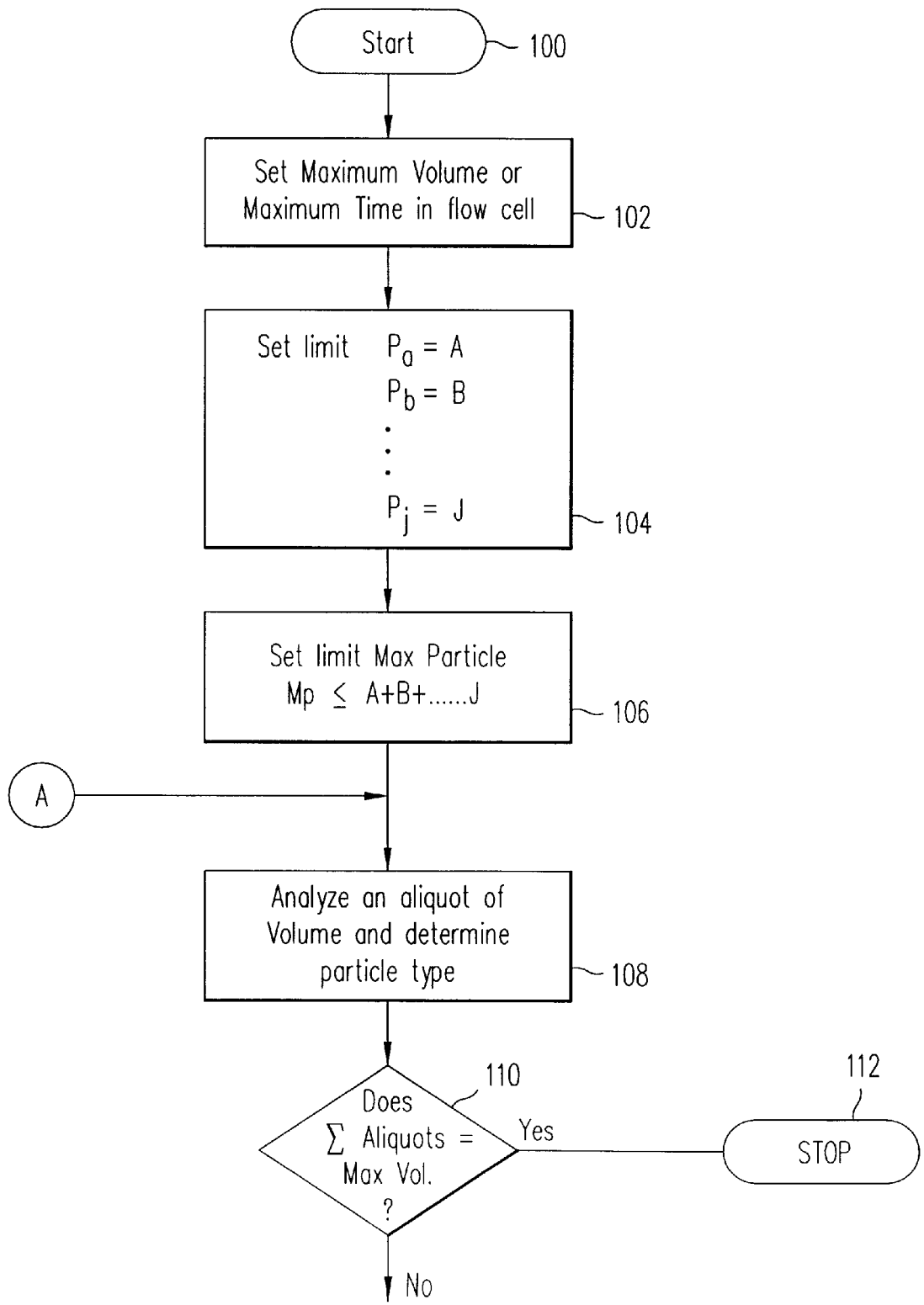
FIG. 4(a & b) is a flowchart of the method of the present invention.
Figure 4B:
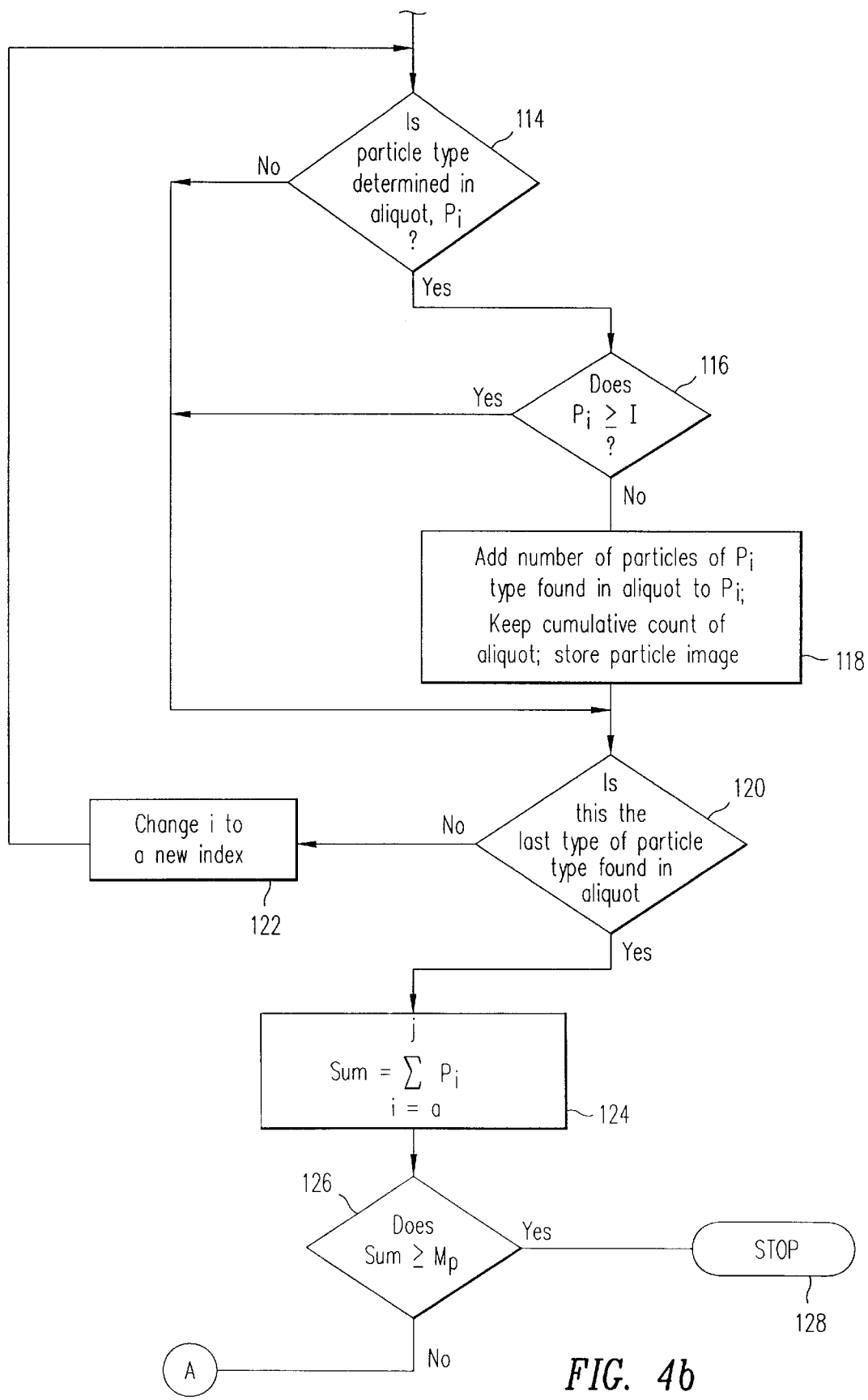

Each electronic image from the camera 34 is stored in the Frame Grabber and Memory 40. The CPU 46 can execute well known software to process the electronic image of the fluid sample, as imaged by the camera 34, including the determination of the type of particles in the electronic image. In addition, the CPU 46 can execute the software whose flow chart is shown in FIG. 4, which implements the method of the present invention, and which will be explained in greater detail hereinafter. The processed images are stored in the Memory 42 which are supplied to the monitor 52 for display. For long term storage, the images can be stored on a peripheral device such as a floppy disc 62. The prime generator 72 detects the edge of the particle in the electronic image. The operation of the prime generator 72 is the subject of U.S. Pat. No. 4,538,299 and is incorporated herein by reference.

The method of the present invention will now be explained with reference to FIG. 4.

The program that is executed on the CPU 46 begins with the block 100. At step 102, the user sets the maximum volume that the flow cell 20a or the microscopic slide 20 will analyze. In the event of a flow cell 20a, the user can also select the maximum examination volume (by setting the time in which the fluid sample will flow through the flow cell 20a, at a substantially constant rate). In the preferred embodiment, the maximum volume of the fluid sample flowing through the flow cell 20a is set as the maximum number of frames of images taken by the CCD camera 34, with the assumption that each frame of image represents a unit volume of the fluid sample flowing through the flow cell 20a. Alternatively, the maximum volume for the system 10 to analyze or the maximum time under which the fluid sample will flow through the flow cell 20a can be set as a default parameter in the system 10.

At step 104, the limits for each of the different plurality of types of cells are set. Here again, these limits can be set by the user or may be "default" values of the system 10. Thus, for example, if there are J types of different biological particles or cells of interest, each of those types of particles, e.g. $P_a$, $P_b$, ... $P_j$, has a limit of A, B, ... J associated therewith. In one embodiment, the maximum number of particles of a particular type is set based upon a type of display on which the particles are to be displayed (e.g., how many particles can be displayed based upon the display type).

At step 106, the maximum number of particles which the system 10 will analyze is also set. This again, can be set by the user or can be a system default value. The maximum number of particles $M_p$ is set to be less than or equal to the sum of the limits of the individual types of cells set in step 104, although in the preferred embodiment the maximum number of particles $M_p$ is set to be less than the sum of the limits of the individual types of cells set in step 104. In other words, $$M_p < A+B+ \ldots +J$$

This limitation that, in the preferred embodiment, the maximum number of particles be less than the sum of the individual types particles, as will be seen, is so that if the maximum number of particles is set equal to the sum of the limits of the different types of cells, and if those individual particle limits are not reached, then the maximum particle limit will never be reached. In that event, the process will be limited simply by the maximum volume or the maximum time.

At step 108, an aliquot of volume of the fluid sample, is analyzed on the microscopic slide 20, either in a wet mount or in a dry smear, or through the flow cell 20a. The various particles are optically imaged and are converted to an electronic image by the camera 34 and processed by the processor 36. Among the functions as previously discussed, the processor 36 determines the type of the particles imaged under the microscope 31.

Each aliquot examined under the microscope 31 either on the microscopic slide 20 or through the flow cell 20a has a certain volume. At step 110, the program determines whether the sum of all of the aliquots examined thus far equals or exceeds the maximum volume limit set in step 102. If the maximum volume limit has been reached, then the process is terminated at step 112. If the maximum volume has not been reached, then the program continues.

At step 114, the number of particles of any particular type that is found by the processor 36 in the aliquot of volume of fluid sample analyzed is then counted for a particular particle type $P_i$.

At step 116, the program determines whether the number of particles counted for a particular type of particle $P_i$ is greater than or equal to the limit set for that particle type in step 104.

If the number of particles for the particle type $P_i$ counted cumulatively is greater than or equal to the limit set in step 104, then the process bypasses step 118 and goes to step 120. If the number of particles for the particle type $P_i$ does not equal to the limit set in step 104, then the number of particles of type $P_i$ found in the aliquot under examination is then added to the cumulative count of the number of particles of $P_i$ found thus far, the image of the particle $P_i$ is stored, along with a count of the cumulative volume (or cumulative frame #) The process then proceeds to step 120.

At step 120, the program determines if this is the last type of particle P found in the aliquot under examination. If it is not, then the subscript or index for the particle type i is changed to a new index in step 122 and the loop reverts back to step 114 for a determination of a different type of particle that has been determined in the aliquot. Therefore, in this manner, all of the particles in the current aliquot under examination are accounted for and the sum of the type of particles determined under the microscope 31 is then added to their respective count of the particles—provided that the sum of the particles for any particular particle type does not exceed the limit set in step 104. In addition, the particle images are stored along with a cumulative volume (or frame number), corresponding to the aliquot.

At step 124, after all the particles determined under the aliquot of interest have been accounted for, the total number of all the particles examined thus far is determined. This is the sum of all the particles of all the different types found and is determined by the equation $$\text{Sum} = \sum_{i=a}^{j} P_i$$

At step 126, the sum of all the particles is then compared to the maximum number $M_p$ of particles limit 106. If the maximum number $M_p$ of particles 106 is reached, then the process is terminated at step 128. If the maximum number $M_p$ of particles has not been reached, then the process reverts back to step 108 where another aliquot of volume of the sample is analyzed either on the microscope slide 20 or through the flow cell 20a. Therefore, as can be seen from the foregoing, the process is stopped whenever the maximum volume has been reached or the maximum total number of particles examined in all the aliquots exceeds the maximum number of particles set in step 106.

After the method of the present invention has been performed, the processor 36 can calculate the concentration of each type of the particle $P_i$ analyzed. The concentration calculation consists of simply taking the number of particles determined for each type of particle counted, divided by the volume of the fluid sample analyzed for each of the particular type of particle. Thus for example, the maximum volume is set at 1000 frames, the limit for particle type $P_a$ is set at 500, and the limit for particle type $P_b$ is set at 10. The limit for particle type $P_a$ is reached after 500 frames. The number of particles counted for particle type $P_b$ for 1000 frames is 10. The concentration for particle type $P_a$ is 500/500 or 1 particle per frame. The concentration for particle type $P_b$ is 10/1000 or 1 particle per 100 frames.

Similar to the disclosure set forth in Ser. No. 363,394, filed on Dec. 23, 1994, whose specification is incorporated herein by reference, a proportionate amount of each type of different particles analyzed can be displayed on the display means 52 in an ordered array by visually discernible characteristics. The electronic images of the particles of interest are displayed in an ordered array by each of the type of particles classification on the display means 52, with the number of particles within each classification or particle type, so displayed being proportional to the percentage determined of the total number of particles of interest displayed. The total number of particles of interest displayed is proportional to the total number of particles that were classified.

In accordance with the disclosure set forth in U.S. Ser. No. 363,394 filed on Dec. 23, 1994, which is incorporated herein by reference, a user can edit the particles displayed. Thereafter, the processor 36 would recalculate the concentration of the particles based upon the editing step. This would consist of arithmetically adjusting the number of particles of each of the different types based upon the total volume counted, and the volume counted for each particle. Thus, in the above example, after displaying the particles on the display means 52, a technician determined that some particles (for example 5) of type $P_a$ were misclassified, and should have been classified as particle type $P_b$, then the proper concentration for each type of particles would be: $P_a$=495/500 and $P_b$=10/1000+5/500=20/1000. The correction is based upon the cumulative count of the original classification of the particle type $P_a$ and the cumulative volume, at various stages of the analysis.

There are a number of ways to determine the various limits, set in steps 102, 104 and 106. With respect to the limit of the maximum volume, that can be set in one of several different ways. First, the maximum volume can be set based upon the desired throughput of the instrument. Therefore, if economic consideration is the only factor, then the maximum volume for analysis for each sample can be set such that the system 10 can process a desired number of samples per unit time.

A second method is based upon the expected concentration of the various particles. Each of the types of particles has an expected concentration. The expected concentration value for the various particle types can be used to set the maximum volume to be analyzed per sample, subject to other limitations as described hereinafter. One other limitation is the precision of the count. As is well known, the precision of the count or the expected value of the coefficient of variation, Cv, is determined as follows:

$$Cv = \frac{1}{\sqrt{n}} \quad n \text{ is the number of particles counted}$$

From this, it can be seen that the limit for the maximum volume can be determined by the precision of the count desired for the different particle types.

For example, suppose particle type $P_a$ has the highest or largest expected concentration. Suppose one desires a precision of (plus or minus) ten percent (10%) for the count of particle type $P_a$. Based upon the above equation, the minimum number of particles of particle type $P_a$ that must be examined is 100. If the expected concentration of particle $P_a$ is 0.5 particles/frame, then the minimum number of frames is 200.

Another limitation that can be used is the probability of detection. Suppose, particle type $P_e$ has the lowest or smallest expected concentration. It has an expected concentration of 1 particle/200 frames. If only 200 frames were analyzed, then the probability of detecting one or more particles of particle type $P_e$ is only 63.2%. If it is desired to detect one or more particles of particle type $P_e$ with a probability of 95.0%, then the expected number of particles must be 3 and 3*200 frames, or 600 frames should be examined. The following table illustrates the probability of observing the minimum or more of particles in a frame given the true or average number of particles per frame, assuming 100% of the volume is processed.

| Min. # Observed | True number of Particles/Frame | | | | | |
| --- | --- | --- | --- | --- | --- | --- |
| | 1 | 2 | 3 | 4 | 5 | 6 |
| 1 | .6321 | .8647 | .9502 | .9817 | .9933 | .9975 |
| 2 | .2642 | .5940 | .8009 | .9084 | .9596 | .9826 |

This process of determining the maximum value based upon the expected concentration of each of the particles is continued, and the maximum volume is set based upon the greatest calculated maximum value from each of the particle type.

From the foregoing, it can be seen that by using the expected concentration of each of the various types of particles and other limitations, such as precision of the count or the probability of detection, the maximum volume can be determined. Conversely, the maximum volume, the precision of count for each of the different particle types, and the probability of detection for the various different particle types can be optimized to yield values for the limits in steps 102 and 104 to optimize throughput (based upon, e.g. cost constraints), and maintain sufficient statistical accuracy.

One example of using the expected concentration is as follows. For example, for a sample of biological fluid, where the expected concentration of the various types of particles may be $P_a$=having a concentration of 30 particles/frame; $P_b$=having a concentration of 0.3 particles/frame; and $P_c$=having a concentration of 0.1 particles/frame, the desired number of particles to be counted, based upon precision, or other factors, may be, for example: $P_a$=450; $P_b$=30; and $P_c$=30, with a total particle count set at 500. Based upon the expected concentration, the number of expected frames to be analyzed would be 15, 100 and 300 respectively. Thus, the maximum volume set in step 102 would be 300 equivalent volume frames. The limits of the particles set in step 104 would be 450, 30 and 30 respectively. Finally, the maximum number of particles set at step 106 is such that $M_p$ is less than or equal to the sum of 450+30+30 or 510. In this case the maximum $M_p$ is set at 500.

The advantage of the method and apparatus of the present invention is that particles of interest may be selectively emphasized. As can be seen from the foregoing, for example, for particle type $P_c$, the method of the present invention can be used to emphasize the discovery of these particles in a particular sample. The various particle limits may be set to selectively emphasize different particle types.

Alternatively, the limits set forth in step 104 may be based upon an inverse proportion to the concentration of the most populous type of particles.

Finally, the limits set in steps 102, 104 and 106 may be based upon an optimization process of a cost parameter associated with the method. There are three cost functions associated with the method: precision cost, detection cost, and run cost.

Precision cost is the cost incurred for incorrectly estimating the number of a given particle type. This is usually calculated for particles having an expected large number, or populous particle type. It decreases as the number of particles counted increases, since the precision, as measured by the coefficient of variation Cv, improves inversely to the square root of the number of particles counted, discussed previously. Furthermore, at some point there is no further benefit obtained from an increase in precision. Thus, the precision cost (PC) may be expressed as:

$$PC(n) = c - n*(c/p) \text{ if } n \leq p$$
$$= 0, \text{ otherwise}$$

where n is the number of particles counted, p is the maximum number of particles beyond which additional particle count would yield no additional precision benefit, and c is the maximum cost (if n=0).

The detection cost is the cost incurred for failing to detect a particle or a number of particles of a given type. This is usually calculated for least populous particle type, where it is desired simply to detect the presence of one or more particles. Once the probability of detection exceeds a certain value, e.g. 99%, then there is no additional cost. This level of probability of detection may be varied The probability of detection is a function only of the expected concentration (or number of particles). Thus, a simple model for this cost function is a "pulse" function model, which has a fixed cost as long as the particle count is below a given minimum. The cost is zero above this limit. Thus, the detection cost, DC, function is:

$$DC(n) = c \text{ if } n \leq p$$
$$= 0, \text{ otherwise}$$

where n is the number of particles counted, p is the maximum number of particles beyond which detection cost is zero, and c is the fixed cost of detection until the limit is reached.

Finally, run cost is the cost associated with the processing of a frame (or aliquot of volume) of information. In systems where there are many other processes occurring, simultaneously, frame processing cost is not incurred until after a minimum number of frames are processed, since other processes such as specimen preparation would preclude processing the next specimen until after a minimum time interval lapses. Once the minimum time (or minimum number of frames) has elapsed, a constant cost per frame is incurred which yields a linearly increasing cost function of the number of frames processed. The run cost (RC) function is as follows:

$$RC(v) = (v - f)*c \text{ if } v \leq p$$
$$= 0, \text{ otherwise}$$

where v is the number of frames analyzed, f is the number of frames beyond which run cost is incurred, and c is the fixed cost per frame beyond f.

The total cost (TC) for running the analysis would be the sum of DC and PC for each particle, multiplied by their expected concentration, D, plus the RC. Thus:

$$TC(v) = \sum_{i=a}^{j} DC_i(D_i v) + PC_i(D_i v)$$

The maximum number of frames to be analyzed, can be calculated based upon the value of v that would minimize the total cost TC.

As can be seen from the foregoing, with the method and apparatus of the present invention, particles of interest that "normally" would not be detected because of their low concentration, but which are desirable for analysis, may be selectively emphasized resulting in a high probability of detection yet, with the system 10 still operating with high throughput. Although the method of the present invention has been described as being implemented in a flow cell, using liquid fluid samples, clearly the method of the present invention is not so limited. For example, the method can be used with a flow cytometer, impedance counters, powder particle analyzer, and the like, which can analyze gaseous as well as liquid fluids, in which different types of particles with different concentrations are present.

What is claimed:

1. A method of analyzing a fluid sample containing a plurality of different types of particles, said method comprising:
   a) setting a limit for the maximum volume of said fluid sample to be analyzed;
   b) setting a limit for the number of particles for each of said plurality of different types;
   c) taking a volume of said fluid sample and analyzing each particle in said volume of said fluid sample including determining the type thereof;
   d) counting the total volume analyzed;
   e) stopping the method in the event the total volume counted in step (d) equals or exceeds the limit for the maximum volume set in step (a);
   f) testing, for each type of particle in the fluid sample determined in step (c), if the total number of particles determined equals or exceeds the limit for said type set in step (b);
   g) adding the number of particles for each of said type determined in step (c) to the respective total number determined for said type, only if the total number of particles determined for that type does not equal or exceed the limit for said type, set in step (b); and
   h) reverting to step (c) in the event the method is not stopped by step (e).

2. The method of claim 1 further comprising:
   i) calculating the concentration of each type of particles analyzed based upon the volume observed; and j) displaying a proportionate amount of each type of different particles analyzed on a display means.

3. The method of claim 2 further comprising:
k) editing said particles displayed; and
l) recalculating the concentration of the particles calculated in step (i) based upon the editing step (l).

4. The method of claim 2 wherein said recalculating step (l) further comprises:
arithmetically adjusting the number of particles of each different type per the volume counted based upon said editing step (k).

5. The method of claim 1 wherein each of said plurality of different types of particles has an expected concentration.

6. The method of claim 1 wherein said setting step (b) further comprises:
multiplying the expected concentration of the expected most populous type by the limit for the maximum volume set in step (a);
multiplying a multiple of the expected concentration of the expected least populous type by the limit for the maximum volume set in step (a).

7. The method of claim 1 wherein said setting step (a) comprises:
setting a maximum examination volume.

8. The method of claim 7, wherein the step of setting a maximum examination volume includes setting a maximum time limit for said fluid sample flowing substantially constantly through a flow cell.

9. The method of claim 1 wherein said fluid sample is a liquid.

10. The method of claim 1 wherein said fluid sample is a gas.

11. The method of claim 1 further comprising:
calculating the limits of steps (a) and (b) to optimize the analysis.

12. The method of claim 1 further comprising:
displaying, on a display, particles of at least a particular one of said types, the display characterized by a display type;
wherein step b) includes setting the limit for the maximum number of the particles of the at least a particular one of said type based upon the display type.

13. The method of claim 1 further comprising:
i) before the first execution of step (h), setting a limit for the maximum of number of particles to be analyzed, said maximum number being less than or equal to the sum of the limits for each of said different types set in step (b);
j) counting the total number of particles analyzed; and
k) stopping the method in the event the total number of particles counted in step (j) equals or exceeds the limit set in step (i)
wherein step (h) includes reverting to step (c) in the event the method is not stopped by steps (e) or (k).

14. The method of claim 13, further comprising:
calculating the limits of steps (a), (b) and (i) to optimize the analysis.

15. A system for analyzing a fluid sample containing a plurality of different types of particles, said system comprising:
a flow cell having an imaging area for flowing said fluid sample through said imaging area;
an optical imaging means for capturing an optical image of said fluid sample at said imaging area and for converting said optical image into an electronic image;
computer means for receiving said electronic images and for executing a computer program for:
a) setting a limit for the maximum volume of said fluid sample to be analyzed;
b) setting a limit for the number of particles for each of said plurality of different types;
c) analyzing said electronic image to determine the particles therein including the type thereof;
d) counting the number of aliquots of said fluid sample flowing through said flow cell to determine the total volume analyzed;
e) stopping the method in the event the total volume determined in step (d) equals or exceeds the limit for the maximum volume set in step (a);
f) testing, for each type of particle in the fluid sample determined in step (d), if the total number of particles determined equals or exceeds the limit for said type set in step (b);
g) adding the number of particles for each of said type determined in step (c) to the respective total number determined for said type, only if the total number of particles determined for that type does not equal or exceed the limit for said type, set in step (b);
h) reverting to step (c) in the event the method is not stopped by step (e); and
display means for displaying said particles analyzed.

16. The system of claim 15 wherein said computer program for further causing the display of a proportionate amount of each type of different particles analyzed to be displayed on said display means and an ordered array by visually discernible characteristics.

17. The system of claim 16 wherein said particles displayed on said display means are displayed with each of said plurality of different types displayed in an ordered array on a display screen means, with the number of particles within each type so displayed being proportional to the concentration determined of the total number of particles of interest displayed, with the total number of particles of interest displayed being proportional to the total number of particles of interest determined.

18. The system of claim 15 wherein said computer program for further causing the calculation of the concentration of each type of particles analyzed based upon the volume observed.

19. The system of claim 18 wherein said computer program for further causing the editing of said particles displayed and for causing the recalculation of the concentration of each type of particles based upon the editing thereof.

20. The system of claim 15, wherein step a) of the computer program, for setting a limit for the maximum volume of said fluid sample to be analyzed, includes setting a maximum time limit for said fluid sample flowing substantially constantly through a flow cell.

21. The system of claim 15, wherein the computer program further comprises the steps of:
i) before the first execution of step (h), setting a limit for the maximum of numbers of particles to be analyzed, said maximum number being less than the sum of the limits for each of said different types set in step (b);
j) counting the total number of particles analyzed;
k) stopping the method in the event the total number of particles counted in step (j) equals or exceeds the limit set in step (i),
wherein step (h) includes reverting to step (c) in the event the program is not stopped by steps (e) or (k).

22. The system of claim 21, wherein the computer program further comprises: calculating the limits in steps (a), (b) and (i) to optimize the analysis.

23. An article of manufacture comprising:
a computer usable medium having computer readable program code embodied therein for execution by a computer, the computer readable program code configured to analyze a fluid sample containing a plurality of different types of particles, the computer readable program code in said article of manufacture comprising:
first computer program code means for setting a limit for the maximum volume of said fluid sample to be analyzed;
second computer program code means for setting a limit for the number of particles for each of said plurality of different types;
third computer program code means for analyzing the particles in an electronic image of said fluid sample including determining the type thereof;
fourth computer program code means for counting the total volume analyzed;
fifth computer program code means for stopping the analysis in the event the total volume counted by said fifth computer program code means equals or exceeds the limit for the maximum volume set by said first computer program code means;
sixth computer program code means for testing, for each type of particle in the fluid sample determined by said fourth computer program code means, if the total number of particles determined equals or exceeds the limit for said type set by said second computer program code means;
seventh computer program code means for adding the number of particles for each of said type determined by said fourth computer program code means to the respective total number determined for said type, only if the total number of particles determined for that type does not equal or exceed the limit for said type, set by said second computer program code means;
eighth computer program code means for reverting to said third computer program code means in the event the analysis is not stopped by said fifth computer program code means.

24. The article of manufacture of claim 23, wherein said computer readable program code in said article of manufacture further comprising:
ninth computer program code means for calculating the concentration of each type of particles analyzed;
tenth computer program code means for displaying a proportionate amount of each type of different particles analyzed on a display means;
eleventh computer program code means for editing said particles displayed; and
twelfth computer program code means for reclassifying the concentration of the particles calculated by said twelfth computer program code means based upon fourteenth computer program code means.

25. The article of manufacture of claim 24 wherein said twelfth computer program code means further comprises:
means for arithmetically adjusting the number of particles of each different type for the total volume determined by the fourth computer program code means based upon said eleventh computer program code means.

26. The article of manufacture of claim 23 wherein each of said plurality of different types of particles has an expected concentration.

27. The article of manufacture of claim 26 wherein said second computer program code means further comprises:
means for multiplying the expected concentration of the expected most populous type by the limit for the maximum volume set by said first computer program code means;
means for multiplying a multiple of the expected concentration of the expected least populous type by the limit for the maximum volume set by said first computer program code means.

28. The article of manufacture of claim 23 wherein said first computer program code means comprises:
means for setting a maximum examination volume.

29. The article of manufacture of claim 28, wherein the means for setting maximum examination volume comprises:
means for setting a time limit for said fluid sample to flow substantially constantly through a flow cell.

30. The article of manufacture of claim 23, wherein the computer readable program code further comprises:
ninth computer program code means for setting a limit for the maximum of numbers of particles to be analyzed, said maximum number being less than the sum of the limits for each of said different types set by said second computer program code means;
tenth computer program code means for counting the total number of particles analyzed; and
eleventh computer program code means for stopping the analysis in the event the total number of particles counted by said ninth computer program code means equals or exceeds the limit set by said third computer program code means
wherein said eighth computer program code means includes reverting to said third computer program code means in the event the program is not stopped by the fifth computer program code means or the eleventh computer program code means.

31. The article of manufacture of claim 30, wherein the computer readable program code further comprises:
computer program code means for calculating the limits in the first, second and ninth computer program code means to optimize the analysis.

32. A method of determining the maximum volume of fluid sample for analysis, wherein said fluid sample has a plurality of different types of particles, with each of said plurality of different types of particles has an expected concentration, said method comprising:
calculating the maximum volume for one or more of said plurality of types of particles based upon its expected concentration, and the desired precision of count; and
selecting the greatest maximum volume calculated for each of the types of particles, as the maximum volume.

33. The method of claim 32 further comprising the step of:
calculating the maximum volume for one or more of said plurality of types of particles based upon its expected concentration, and the probability of detection desired.

34. The method of claim 32, wherein said method further comprising the step of:
calculating a parameter associated with the analysis of each of type of particles; and
wherein said selecting step comprises selecting said greatest volume calculated based upon an optimization of said parameter calculated.

35. The method of claim 34 wherein said parameter is cost.

* * * * *